United States Patent [19]

Vinson et al.

[11] 4,022,880

[45] May 10, 1977

[54] ANTICALCULUS COMPOSITION

[75] Inventors: Leonard J. Vinson, Glen Rock; Lewis P. Cancro, River Vale, both of N.J.

[73] Assignee: Lever Brothers Company, New York, N.Y.

[22] Filed: Aug. 11, 1975

[21] Appl. No.: 603,826

Related U.S. Application Data

[63] Continuation of Ser. No. 401,001, Sept. 26, 1973, which is a continuation of Ser. No. 194,573, Nov. 1, 1974, abandoned, and a continuation-in-part of Ser. No. 879,931, Nov. 25, 1969, abandoned.

[52] U.S. Cl. .................................. 424/49; 424/50; 424/24; 424/55
[51] Int. Cl.² .......................................... A61K 7/16
[58] Field of Search ................................ 424/49–58

[56] References Cited

UNITED STATES PATENTS

| | | | |
|---|---|---|---|
| 1,488,097 | 3/1924 | Creger | 424/55 |
| 1,861,189 | 5/1932 | Pasternack | 424/55 |
| 2,723,217 | 11/1955 | Gershon et al. | 424/57 |
| 3,095,356 | 6/1963 | Moss | 424/51 |
| 3,538,230 | 11/1970 | Pader et al. | 424/50 |
| 3,622,662 | 11/1971 | Roberts et al. | 424/54 |

FOREIGN PATENTS OR APPLICATIONS

| | | | |
|---|---|---|---|
| 1,504,155 | 10/1967 | France | 424/54 |
| 1,427,290 | 12/1965 | France | 424/54 |
| 478,570 | 11/1969 | Switzerland | 424/56 |
| 689,679 | 4/1953 | United Kingdom | 424/58 |
| 1,166,627 | 10/1969 | United Kingdom | 424/54 |

OTHER PUBLICATIONS

Chemical Abstracts (1), vol. 70, entry 1141 08s, 1969 citing Vedernikov et al., *Sb. Tr. Les. Khoz. (Kazan)*, 1967, No. 17, pp. 221–239.
Sprowls et al., J.A.P.A., vol. 32, pp. 33–40, 1943.
*Chemical Abstracts*, vol. 67, entry 74741x, 1967 (2).

*Primary Examiner*—Lewis Gotts
*Assistant Examiner*—Cary Owens
*Attorney, Agent, or Firm*—James J. Farrell; Kenneth F. Dusyn; Melvin H. Kurtz

[57] ABSTRACT

This invention relates to an improved composition for inhibiting dental plaque and calculus formation, comprising zinc ions and a non-toxic, organoleptically acceptable antibacterial agent in an orally acceptable medium, and to a process for retarding the growth of dental plaque and calculus by application to the teeth of the above composition.

20 Claims, No Drawings

ANTICALCULUS COMPOSITION

This application is a continuation of Ser. No. 401,001, filed Sept. 26, 1973, which is a continuation of Ser. No. 194,573, filed Nov. 1, 1971, now abandoned, and a continuation-in-part of Ser. No. 879,931, filed Nov. 25, 1969, now abandoned.

BACKGROUND OF THE INVENTION

The present invention relates to oral compositions containing a zinc compound capable of furnishing zinc ions in the oral cavity, and an antibacterial agent, for use in the mouth to retard the accumulation of dental plaque and/or calculus.

Dental plaque forms as a film on teeth. It is a product of microbial growth, a dense microbial layer consisting of a mass of microorganisms embedded in a matrix, which accumulates on the tooth surfaces. The microorganisms are mainly coccoidal organisms, particularly in early plaque, which, in the mouths of some persons at least, change to filamentous organisms after a few days.

A wide variety of microorganisms are found in the oral cavity, among these being gram-positive anaerobic rods presumably comprising *Corynebacterium, Actinomyces,* and *Propionibacterium, Neisseria, Nocardia, Fusobacterium, Veillonella,* and *Streptococci,* such as *S. mutans, S. bovis, S. salivarius,* and gram-positive *streptococci* of the genus *Peptostreptococcus* (See Robert J. Fitzgerald in "The Alabama Journal of Medical Sciences" Volume 5, No. 3, July, 1968, pp. 241-242).

Bacteria associated with dental plaque and the development of calculus incude *Streptococci, Corynebacterium,* and filamentous *Nocardia*-like organisms. These are gram-positive organisms.

In addition to the aforementioned microorganisms, there are present in plaque relatively small amounts of other substances such as salivary proteins, carbohydrates, epithelial cells, and leucocytes.

Dental plaque has been observed to form following a dental prophylaxis, due to bacteria which grew out of defects in the tooth enamel where they had resided and remained unaffected by the prophylaxis treatment.

Plaque may form on any part of the tooth surface, and is found particularly at the gingival margin, in cracks in the enamel, and on the surface of dental calculus.

The importance of giving consideration to the action of plaque on the teeth lies in the tendency of plaque to produce gingivitis and perhaps other types of periodontal disease, as well as dental caries and dental calculus.

Dental plaque is a precursor of dental calculus. The latter forms from the plaque that accumulates on the teeth in the form of a hard mineralized deposit. It is particularly prone to form at the gingival margin, i.e., the junction of the tooth and gingiva. Both the bacterial and non-bacterial components of plaque are mineralized to form calculus, which comprises, in addition to mineralized bacteria, organic constituents, such as epithelial cells, live bacteria, salivary proteins, leucocytes, and crystals of substances having molecularly bound calcium and phosphorus, e.g., hydroxyapatite, $3[Ca_3(PO_4)_2]\cdot Ca(OH)_2$, octacalcium phosphate, $Ca_8(HPO_4)_2(PO_4)_4\cdot 5H_2O$, brushite, $CaHPO_4\cdot 2H_2O$, and whitlockite, which is considered to have the formula beta-$Ca_3(PO_4)_2$.

Calculus, like plaque, is considered to be a prime causative factor in periodontal disease.

Regular tooth brushing with a conventional dentifrice may, for some persons, greatly retard or even prevent the accumulation of calculus. For other persons however calculus builds up rapidly even with regular brushing. Removal by a dentist is currently the only safeguard against serious gingival inflammation which can be caused by dental calculus.

THE INVENTION

It has now been discovered that the rate of development of dental plaque and calculus can be greatly retarded by contacting the teeth with a combination of zinc ions and a antibacterial agent. This combination may comprise one or more zinc salts furnishing zinc ions and one or more antibacterial agents.

Thus in accordance with one aspect of the present invention, a composition comprising a water-soluble zinc salt and an antibacterial agent, which has the ability to retard the formation of calculus on teeth may be caused to contact the teeth to retard the growth of dental calculus thereon.

In another aspect, the invention comprises an anticalculus composition, suitable for retarding the accumulation of dental calculus, comprising zinc ions and an antibacterial agent in an orally acceptable medium.

An additional aspect embodies an anticalculus composition for retarding the accumulation of dental calculus,, comprising a zinc salt which furnishes zinc ions in the mouth and an antibacterial agent capable of inhibiting the growth of gram-positive oral microflora, in an orally acceptable medium.

In another embodiment, the invention comprises a water-soluble zinc salt and an antibacterial agent in a compatible toothpaste composition.

In a further embodiment the invention comprises a water-soluble zinc salt and an antibacterial agent in a mouthwash, or oral rinse.

In a still further embodiment, the invention comprises a polishing agent and an anticalculus composition comprising a zinc salt and an antibacterial agent.

The combination of zinc ions and antibacterial agent is ordinarily incorporated in oral compositions such as mouthwashes, toothpastes, tooth powders, or simple diluents.

The essential components of the invention are the orally acceptable medium and the anticalculus mixture of zinc ions and an antibacterial agent. By the term "orally acceptable medium" we are referring to any carrier medium for the anticalculus mixture that is harmless to the oral cavity and not intentionally swallowed, but harmless in an amount accidentally ingested during use.

THEORY OF THE INVENTION

Although we do not wish to be held to any theory expressed herein, we postulate that zinc ions interfere with calcium uptake of the saliva and with crystallization of the calcium compounds in the plaque, and thus retard the formation of hydroxyapatite crystals, a necessary constituent of dental calculus. Without an antibacterial agent however, the bacterial masses normally found in the mouth produce plaque deposits which could ultimately mineralize once nucleated.

An antibacterial agent alone kills or retards the growth of plaque bacteria, but in the absence of zinc ions, the remaining dead bacteria mineralize to form calculus. Neither zinc ions nor an antibacterial agent then produces the technical effect possible with the two in combination. The excellent results obtained with a combination of zinc ions and an antibacterial agent are attributed to their cooperating effect on the teeth. The zinc ions act as crystallization inhibitors and interfere with nucleation; the antibacterial agents interfere with bacterial colonization of the plaque; when zinc ions and an antibacterial agent are used together, the zinc ions co-act to keep the plaque porous and more penetrable by the antibacterial agent.

THE PRIOR ART

Prior to our invention, attempts have been made by others to retard the accumulation of dental calculus by means of zinc salts. M. T. Hanke in the Journal of the American Dental Association, Volume 27, September, 1940, page 1388, describes experiments to combat plaque with mouthwashes containing a variety of metallic salts, including zinc salts, having antifungal properties. The work of Hanke leads to the conclusion that the use of a zinc salt as the sole therapeutic agent has serious drawbacks, in view of the disclosure that zinc salts are not effective in all cases, and that zinc acetate does not show any significant bactericidal action in the mouth.

Also known is the use of soluble zinc salts as germicidal and deodorizing compounds, as set forth in U.S. Pat. No. 1,593,485 to Crosnier. This patent discloses that mixtures of zinc sulfophenate (i.e., phenolsulfonate) and zinc sulfate, chloride, or acetate are useful as bactericides and deodorants, the latter property being of value in slaughter-houses and the like where hydrogen sulfide is generated. However, there is no suggestion in this patent, nor in any other art known to the inventors, that a combination of zinc ions and an antibacterial agent has antiplaque and/or anticalculus properties.

Antibacterial agents also have been tested for their effect on calculus. H. R. Muhlemann, in "Evaluation of Agents Used in the Prevention of Oral Disease", a series of papers published in "Annals of the New York Academy of Sciences" Volume 153, Art. 1, December 23, 1968, pages 164–196, describes the testing of some antibacterial agents in mouthwashes for their anticalculus effect. Muhlemann's observation that the rate of deposit mineralization proceeds undisturbed despite the presence of antibacterial compounds (although formation of plaque is reduced) is an indication of the unsatisfactory nature of the action of antibacterial compounds on plaque and calculus.

In U.S. Pat. No. 3,342,687 to D. H. Gould, there is disclosed an antimicrobial agent, defined by physical characteristics, used either alone or with a second antimicrobial agent in oral preparations to decrease the formation of plaque and calculus.

J. B. Sprowls and C. F. Poe have disclosed mixtures of one of four antiseptics, namely phenol, hexylresorcinol, merthiolate, and metaphen, each with several astringent compounds, including zinc compounds (see J. Amer. Pharm. Assoc., Vol. XXXII, 33–40, February, 1943). These investigators reported that the germicidal efficiency of the above-mentioned antiseptics is increased by many astringent salts, including some zinc salts. Nothing was reported however, on the plaque or calculus problem.

P. Gjermo et al in U. Periodont. Res. 5, 102–109, 1970 disclose that chlorhexidine gluconate and chlorhexidine acetate almost completely inhibited plaque formation in in vivo tests.

It will be understood that our discovery concerns the co-action of zinc ions and an antibacterial agent, rather than a well-defined synergistic property. Neither a zinc compound nor an antibacterial agent alone provides the most effective anticalculus action. The use of high levels of either agent alone would not produce the desired effect. Moreover, high levels of a zinc compound would be too stringent, and high levels of antibacterial agent may interfere with the action of beneficial bacteria in the mouth. By using mixtures of the two classes however advantage is taken not only of their co-action, but also of the fact that low levels of each class can be employed, i.e., levels sufficiently low to be orally acceptable, while at the same time providing, by their combination, highly effective anticalculus activity.

The prior-art disclosures indicate that calculus or plaque accumulation has been retarded by certain zinc salts alone or antibacterial agents alone. Applicants have made direct measurements of calculus reduction and have noted that in general the prior-art compositions, i.e., zinc compounds alone or antibacterial agents alone, provide only about one-half the protection afforded by the compositions of the invention. The extent of reduction of accumulation of dental calculus and plaque by zinc compounds alone and by antibacterial agents alone as compared with combinations thereof is shown in tables 1 and 2. The regarding of the growth of calculus on teeth in the human oral cavity is demonstrated by tests described in Example 1, wherein the reduction in calculus accumulation on human teeth after using a product of the invention for two consecutive 3-month periods is measured, and in Example 2 wherein the weight of deposits accumulated on a strip of Mylar in the mouth is measured.

Zinc ions may be furnished by any physiologically acceptable zinc salt having a measurable solubility in water. The effective portion of the zinc salts are the zinc ions, i.e., zinc cations. The remainder of the molecule of the zinc salt may be inert for anticalculus purposes. Thus it is immaterial which of the many possible zinc compounds is used, so long as it is capable of furnishing zinc ions within the range of proportions required by the invention. For present purposes zinc compounds are classified with respect to solubility as "soluble" if the compounds are soluble in water to the extent equivalent to at least about 1 gram of Zn per 100 ml of water at about 25° C, and as "slightly soluble" at lower solubilities. It is preferred to use the slightly soluble zinc compounds. A particularly preferred zinc compound is zinc phenolsulfonate, because it is virtually insensitive to pH change, for example to the adjustment of the pH of a mouthwash to near neutrality, with respect to hydrolysis and precipitation.

The role of zinc phenolsulfonate in the compositions of the present invention is that of a zinc compound to furnish zinc ions. Although U.S. Pat. No. 1,593,485 to Crosnier refers to zinc phenolsulfonate as a very powerful bactericide this compound does not have the type of antibacterial action required of the antibacterial agents of the invention and does not fall within the definition of the claimed antibacterial agents, that is, it does not fulfill the requirement that the antibacterial agent must be capable of inhibiting the growth of gram-positive microflora for at least about 3 hours.

If the antibacterial agent is used within the required percentage range in the form of its zinc derivative, its zinc content is normally too low to furnish the required concentration of zinc ions in the absence of another zinc salt, and it is preferred that the zinc salt used to furnish zinc ions and the antibacterial agent be separate and distinct compounds.

In view of the facts presented in the foregoing discussion it is possible, in some instances, to meet the zinc ion requirements with a minimum use of extraneous and inert anion of the zinc compound by employing a zinc derivative of the antibacterial agent.

THE ANTICALCULUS MIXTURE

The mixture may comprise one or more zinc salts, or zinc ions therefrom, along with one or more antibacterial agents.

Examples of zinc compounds that may be employed are zinc salts of the following organic and inorganic anions: acetate, benzoate, borate, bromide, carbonate, citrate, chloride, glycerophosphate, hexafluorosilicate, dl-lactate (trihydrate) nitrate, phenolsulfonate, silicate, alkanoates having 8 to 18 carbon atoms, such as zinc stearate, salicylate, stannate, sulfate, tannate, titanate, tetrafluoroborate, oxide, peroxide, tartrate, etc. The zinc compounds may be used singly or in admixture.

By the term "zinc ion" as used herein, we are referring to the Zn portion of a zinc compound capable of dissociating into zinc ions at a temperature of about 37° C, as well as to zinc ions formed in aqueous medium such as a mouthwash or oral salivary secretions.

The orally acceptable medium may be a polishing agent, water, a toothpaste, tooth powder, mouthwash, or a composition designed for topical application by a dentist.

The several components will be so selected as to kind and amount to insure that the whole composition will be non-injurious to the oral cavity, and harmless to the human system if small amounts are accidentally ingested during use. The component most likely to be injurious is the antibacterial agent, and it will be understood, with regard to this agent in particular, that it will be present in non-toxic proportions.

In general, the proportion of zinc compound will be kept at a minimum effective level to avoid undue astringency. The level can be higher for the more insoluble compounds. The zinc compounds referred to as "slightly soluble" have sufficient, although in some instances almost negligible, solubility in water to furnish zinc ions. The zinc compounds may be present in the compositions in amounts sufficient to furnish about 0.05% to about 4%, or preferably about 0.05% to about 1.0%, zinc ion.

The slightly soluble zinc compounds such as zinc citrate or zinc oxide, may be present within a range of proportions equivalent to about 0.05% to about 4% Zn ion, preferably about 0.2% to about 1.5%, while a soluble zinc compound, for example zinc chloride, will usually be present in lesser proportions, for example in amounts equivalent to about 0.05% to about 0.5% Zn ion, preferably about 0.1% to about 0.25%. The antibacterial agent may be present from about 0.03% to about 0.5%, or preferably from about 0.05% to about 0.2%.

As used herein, the term "antibacterial agent" refers to a wide variety of substances having germicidal action, such as the halogenated salicylanilides, halogenated carbanilides, halogenated bisphenols, alkylbenzoylacrylates, quaternary ammonium compounds, thiuram sulfides, dithiocarbamates, antibiotics, halogenated diphenyl ethers, halogenated anilides of thiophene carboxylic acids, and chlorhexidines.

Among the halogenated salicylanilides there may be mentioned the following derivatives:

5-bromo-salicylanilide
4',5-dibromo-salicylanilide
3,4',5-tribromo-salicylanilide
6-chloro-salicylanilide
4'5-dichloro-salicylanide
3,4'5-trichloro-salicylanilide
4',5-diiodo-salicylanilide
3,4',5-triiodo-salicylanilide
5-chloro-3'-trifluoromethyl-salicylanilide
5-chloro-2'-trifluoromethyl-salicylanilide
3,5-dibromo-3'-trifluoromethyl-salicylanilide
3-chloro-5-bromo-4'-trifluoromethyl-salicylanilide
2',5-dichloro-3-phenyl-salicylanilide
3',5-dichloro-4'-methyl-3-phenyl-salicylanilide
3',5-dichloro-4'-phenyl-3-phenyl-salicylanilide
3,3',5-trichloro-6'-(p-chlorophenoxy)-salicylanilide
3',5-dichloro-6'-(p-bromophenoxy)-salicylanilide
3,5-dichloro-6'-phenoxy-salicylanilide
3,5-dichloro-6'-(o-chlorophenoxy)-salicylanilide
5-chloro-6'-beta-naphthyloxy-salicylanilide
5-chloro-6'-alpha-naphthyloxy-salicylanilide
3,3',4-trichloro-6'-beta-naphthyloxy-salicylailide;

Halogenated carbanilides are represented by the 3,4,4'-trichloro-carbanilide and the 3,3',4-trichloro derivatives and by 3-trifluoromethyl-4,4'-dichlorocarbanilide.

The bis-phenols are represented by the following:

2,2'-methylenebis (4-chlorophenol)
2,2'-methylenebis(4,6-dichlorophenol)
2,2'-methylenebis(3,4,6-trichlorophenol)
2,2'-thiobis(4,6-dichlorophenol)
2,2'-diketobis(4-bromophenol)
2,2'-methylenebis(4-chloro-6-isopropylphenol)
2,2'-isopropylidenebis(6-sec-butyl-4-chlorophenol)

The useful alkylbenzoyl acrylates comprise the [sodium salts of alkylbenzoylacrylic acids wherein the alkyl portion has from about 5 to about 12 carbon atoms.];

Examples of quaternary ammonium compounds are:
diisobutylphenoxyethoxyethyldimethylbenzylammonium chloride
diisobutylcresoxyethoxyethyldimethylbenzylammonium chloride
N-methyl-N-(2-hydroxyethyl)-N-(2-hydroxydodecyl)-N-benzyl ammonium chloride
Cetyl trimethylammonium bromide
Stearyl trimethylammonium bromide
Oleyl dimethylethylammonium bromide
Lauryldimethylchlorethoxyethylammonium chloride
Lauryldimethylbenzylammonium chloride
Alkyl ($C_8$–$C_{18}$)dimethyl(3,4-dichlorobenzyl)-ammonium chloride
Lauryl pyridinium bromide
Lauryl isoquinolinium bromide
N(lauroyloxyethylaminoformylmethyl)pyridinium chloride;

Examples of the thiocarbamates and the thiuram sulfides are:

disodium ethylene bis-dithiocarbamate (Nabam)

diammonium ethylene bis-dithiocarbamate (amabam)
Zn ethylene bis-dithiocarbamate (ziram)
Fe ethylene bis-dithiocarbamate (ferbam)
Mn ethylene bis-dithiocarbamate (manzate)
Zinc N-sec-butyl-N-ethyl dithiocarbamate
tetramethyl thiuram disulfide
  tetrabenzyl thiuram disulfide
tetraethyl thiuram disulfide
tetramethyl thiuram sulfide It will be understood that the compositions of this invention may be used outside the mouth for the cleaning of dentures or the like, and that when the compositions are thus used, there is a wider latitude in the choice of antibacterial agent than when the compositions are used in the mouth. Those skilled in the art will recognize that some of the aforementioned antibacterial agents may not, for organoleptic reasons, be as desirable as others for use in the mouth. It will be recognized too, that some of the aforementioned antibacterial agents may be too costly for large-scale commercial use. In general, the preferred antibacterial agents fall within the subgeneric groups of halogenated salicylanilides, halogenated carbanilides, halogenated bis-phenols, halogenated hydroxydiphenyl ethers, and alkylbenzoyl acrylates.

From the viewpoint of safety, effectiveness, and organoleptic acceptability, we prefer the following specific antibacterial agents:
4',5-dibromosalicylanilide
the zinc derivative of 4',5-dibromosalicylanilide
3,4',5-tribromosalicylanilide
the zinc derivative of 3,4',5-tribromosalicylanilide
3,4',5-trichlorosalicylanilide
the zinc derivative of 3,4',5-trichlorosalicylanilide
3,5-dibromo-4'-trifluoromethylsalicylanilide
the zinc derivative of 3,5-dibromo-4'-trifluoromethylsalicylanilide
3,4,4'-trichlorocarbanilide
3-trifluoromethyl-4,4'-dichlorocarbanilide
2,2'-methylenebis(3,4,6-trichlorophenol)
the zinc derivative of 2,2'-methylenebis (3,4,6-trichlorophenol)
2,4,4'-trichloro-2'-hydroxydiphenyl ether
Sodium dodecylbenzoyl acrylate
Tyrothricin
N-methyl-N-(2-hydroxyethyl)-N-(2-hydroxydodecyl)-N-benzylammonium chloride
Especially preferred are:
3,4'5-tribromosalicylanilide
the zinc derivative of 3,4'5-tribromosalicylanilide
chlorhexidine digluconate
chlorhexidine diaceate
chlorhexidine is 1,1'-hexamethylenebis (5-(para-chlorophenyl)biguanide)
4',5-dibromosalicylanilide
the zinc derivative of 4',5-dibromosalicylanilide
3,4,4'-trichlorocarbanilide
2',4,4'-trichloro-2-hydroxydiphenyl ether It has been found advantageous to form a complex of the antibacterial agent or the zinc compound with a particulated organic polymer carrier, such as polyethylene, polypropylene, polystyrene, polyacrylic resins, polyesters, polyamide resins, and the particulated thermosetting resins such as the melamine, epoxy, and phenol-formaldehyde resins, or with an inorganic polishing agent suitable for use in a dentifrice.

Among the suitable inorganic polishing agents useful in accordance with the invention are silica xerogels and silica aerogels manufactured by the Davison Chemical Division of W. R. Grace and Co. under the tradenames of Syloid 63, Syloid 65 (xerogels) and Syloid 244 (aerogel). The xerogels are synthetic, aggregated, amorphous, highly porous silicas having generally a mean particle diameter of about 4 to 10 microns. The aerogel Syloid 244 has a mean particle diameter of about 3 microns and is less porous than are the xerogels. Also useful are other polishing agents disclosed hereinafter.

The finer particles of polymer or other substances serve as a carrier, and prevent coagulation of the antibacterial agent in liquid media. The fine particles having the antibacterial agent attached thereon may be used in place of the antibacterial agent in any of the compositions of the invention.

The carrier should be in the form of fine particles of such size that at least 40% pass through a 325 mesh screen, and at least 90% pass through a 20 mesh screen. The finer particles within this size range are preferred, particularly a size distribution such that all the particles pass through a 20 mesh screen, more than 90% pass through a 100 mesh screen, more than 80% pass through a 200 mesh screen, and more than 40% pass through a 325 mesh screen. Especially preferred are the finer particles having a mean particle diameter of about 3 to about 44 microns.

A particularly useful polymer is polyethylene in powder form of such size that more than 40% passes through a 325 mesh screen, more than 80% passes through a 200 mesh screen, at least 85% passes through a 100 mesh screen, and 90 to 100% passes through a 20 mesh screen. Such polyethylene polymers are sold under the names of Super Dylan polyethylene J-1 or J-2 powder.

Compatible mixtures of two or more of the germicides may be used. An example of a useful germicidal mixture is a commercially available mixture of 4'5-dibromosalicylanilide and 3,4',5-tribromosalicylanilide in about equal proportions, or the zinc derivatives thereof.

THE POLISHING AGENTS

The polishing agents suitable for use in the compositions of the invention will be those that are compatible with the anticalculus mixture of zinc ions and an antibacterial agent, and will be in particulate form. Among the polishing agents in particulate form suitable for use in toothpaste or tooth powder compositions of the invention are alpha-alumina, alumina trihydrate, silica, silica gels, polyethylene, magnesium carbonate, thermosetting synthetic resins, such as the polymerized melamines (e.g., melamine-formaldehyde), phenolics, (e.g., phenol-formaldehyde), ureas (e.g., urea-formaldehyde), melamine-ureas, cross-linked epoxies and cross-linked polyesters, as described in U.S. Pat. No. 3,070,510 to William E. Cooley.

Polishing agents will be present in the toothpastes of our invention over the broad range of about 1% to 70%, preferably 10% to 60%, and typically from about 40% to 50%. In a tooth powder the polishing agent will be present over the range of about 50% to 99%, preferably about 70% to 95%, and typically from about 90% to about 95%.

OTHER COMPONENTS

The toothpastes will usually contain bodying agents such as gum Karaya, gum Tragacanth, starch, sodium carboxymethylcellulose, Irish moss, gum arabic, sodium carboxymethylhydroxyethylcellulose, polyvinylpyrrolidone, etc. When present, these will usually be at levels of from about 0.5% to about 3%, preferably from about 0.8% to about 1.5%.

Humectants are desirable in a toothpaste. These will usually be such compounds as glucose, honey, glycerol, propylene glycol, sorbitol, polyethylene glycol 400, and other polyhydric alcohols, and may be present in the composition in amounts up to about 35% by weight.

Other adjuvants may be present, such as fluorine compounds, chlorophyll compounds, flavor substances, saccharin, urea, ammonium compounds, alcohol, mineral oil, foaming agents or detergents, such as sodium lauryl sulfate, dodecanesulfonate, acyl taurines, acyl isethionates, etc., depending upon the form of the product.

The orally acceptable medium may be a mouthwash comprising water with optionally alcohol, a wetting agent, colorants, flavor substances, sweeteners, etc. Thickening agents may be added if desired, to aid in suspending any of the less soluble components that may be present.

SCOPE OF THE INVENTION

The invention encompasses compositions having about 0.05% to about 4% zinc ions in combination with about 0.03% to about 0.5% of a non-toxic, organoleptically acceptable antibacterial agent having bacteriostatic proportions and capable of inhibiting the growth of gram-positive oral microflora for at least about three hours, in an orally acceptable medium.

In order that the invention may be fully understood, the several embodiments are particularly described in the following Examples.

EXAMPLE 1

The antibacterial agent may be complexed with a particulate polymer carrier, and the complex unstably suspended to form an oral rinse. The following composition is exemplary.

|  | % |
|---|---|
| Zn phenolsulfonate | 1.00 |
| Zn TBS/polyethylene powder* | 0.25 |
| Flavor | 0.15 |
| Saccharin | 0.02 |
| FD&C Yellow No. 6 (0.7% solution) | 0.10 |
| FD&C Red No. 2 (0.2% solution) | 0.12 |
| Water | 98.36 |
|  | 100.00 |

*1 part by weight of zinc 3,4',5-tribromosalicylanilide complexed with 1 part by weight of particles of Super Dylan J-1 (polyethylene powder over 90% of which passes through a 20 mesh screen, and over 40% of which passes through a 325 mesh screen).

The effectiveness of this composition in retarding the growth of dental calculus was determined clinically by a panel consisting initially of 100 male human subjects and ending with 73 in phase II (as described hereinafter), and 61 in phase III (as described hereinafter), the loss being due to voluntary and unavoidable withdrawal from the panel. Each member of the panel was given an oral prophlaxis after having been chosen from a group of subjects previously selected on the basis of oral history, amount of calculus accumulations at the time of examination, general hygiene of the mouth, cleanliness of teeth, brushing habits, elapsed time since the last prophylaxis, etc. In order to insure proper participation by the subjects, they were instructed in proper procedures of oral care.

Phase I The subjects were furnished a placebo oral rinse composition, a standard toothbrush and a standard commercial dentifrice (Pepsodent, a composition comprising dicalcium phosphate dihydrate as the principal polishing agent, humectant, and other common dentifrice ingredients). The subjects were instructed to use the two products at least twice a day. At the end of the period of three months the calculus scores of the subjects were determined by the Volpe-Manhold method (J. Periodontology, Volume 36, page 292 (1965)).

Phase II The subjects remaining in the panel at the end of phase I were then divided into two comparable groups of 37 and 36 persons, balanced with respect to calculus baseline scores measured after three months' usage of the placebo products. They were then given a second oral prophylaxis. One group having an average baseline calculus score of 13.7 was allowed to continue on their original oral hygiene routine, i.e., Pepsodent toothpaste plus a placebo mouthwash. The other group having an average baseline calculus score of 13.1 was instructed to continue the use of the dentifrice, but instead of the placebo oral rinse was supplied with an oral rinse having the composition of Example 1. After three months on this regimen the subjects were scored for calculus formation.

Phase III The subjects remaining in the panel at the end of phase II were finally given another oral prophylaxis and the procedure repeated. Because of additional withdrawals of panelists, the average baseline scores were recalculated for those remaining. The 30 panelists remaining in the group using the placebo rinse had a new baseline score of 14.0 for phase III, the second 3 month test period, while the 31 panelists remaining in the group using the mouthwash of the invention retained the original baseline score, i.e., 13.1. The results are shown in Table 1.

TABLE 1

| MEAN CALCULUS SCORES AND PERCENT REDUCTION OF CALCULUS | | | | | |
|---|---|---|---|---|---|
| | At the End of Phase II | | | At the End of Phase III | |
| | Calculus Score | % Reduction of Calculus | | Calculus Score | % Reduction of Calculus |
| 37 panelists using Pepsodent Toothpaste + a placebo rinse. (baseline score of 13.7) | 9.3 | 32.1 | 30 panelists using Pepsodent Toothpaste + a placebo rinse and having a recalculated baseline score of 14.0 | 8.9 | 36.3 |
| 36 panelists using Pepsodent + the oral rinse of Example | 3.7 | 71.8 | 31 panelists using Pepsodent Toothpaste | 4.2 | 63.5 |

TABLE 1-continued

MEAN CALCULUS SCORES AND PERCENT REDUCTION OF CALCULUS

| | At the End of Phase II | | At the End of Phase III | |
|---|---|---|---|---|
| | Calculus Score | % Reduction of Calculus | Calculus Score | % Reduction of Calculus |
| 1. (baseline score of 13.1) | + the oral rinse of Example 1 and having a recalculated baseline score of 13.1 | | | |

EXAMPLE 2

In addition to showing the effectiveness of our anticalculus agent by the clinical evaluation procedure of example 1, a "Mylar Strip Assay" in vivo evaluation was made by the procedure described below. It is evident, using this test also, that the combination of zinc ions and an antibacterial agent is highly effective in reducing calculus formation.

The Mylar Strip Assay is an indication of the ability of an agent to inhibit calculus accumulation, primarily in the early stages of its formation. Like the clinical assay procedure described above, it employs human subjects and, therefore, is relatively very close to the actual human experience. It has been used by many experts in the dental research field as a means of studying calculus formation and ways for the inhibition thereof.

In this technique contoured, roughened, preweighed polyester strips are attached by means of ligatures to the lingual surface of the lower incisor teeth for periods varying from about 4 days to 10 days or more. At the end of the test period the strips are removed and dried for 1 hour at 100° C, and the amount of deposit laid down on the strips during the test period is determined by weighing. During the test period agent (s) may be applied in solution, in suspension, in dentifrice, etc. Care is observed to insure that the strips are not subjected to the action of a toothbrush, since inadvertent brushing could yield spurious results. The test material is applied according to the preset regimen, i.e., two 10 ml rinses per day. Controls are established whereby the effects of a placebo can be determined. The Mylar Strip Assay is generally run in accordance with a crossover design, i.e., half the panel uses the test material first and half the panel uses the placebo first, and then the treatments are reversed.

The deposits accumulated on the strips are considered to represent precalculus plaque and early calculus, depending on the length of time the strips are affixed. The extent to which this material accumulates is evaluated by measurement of dry weight, weight of ash, calcium content, and phosphate content. Since calculus undoubtedly originates from plaque, and is made up in large measure of hydroxyapatite and other mineral materials (as high as 70% mineral in aged samples), reduction in any of the above parameters can be validly interpreted as inhibition of calculus formation.

TABLE 2

MYLAR STRIP (HUMAN SUBJECTS)

| Soluble Zn % | Germicide % | Vehicle | % Red.[g] |
|---|---|---|---|
| Zn Phenolsulfonate 1% | Quaternary 0.1%[a] | Rinse | 32.3% |
| Zn Phenolsulfonate 1% | Zn TBS 0.1%[b] | Rinse | 41.8% |
| Zn Phenolsulfonate 1% | Zn TBS 0.1% | Rinse | 38.8% |
| Zn Phenolsulfonate 1% | Zn TBS 0.25% | Paste | 25.1% |
| Zn Phenolsulfonate 1% | Zn TBS 0.25% | Paste | 24.3% |
| Zn Phenolsulfonate 1% | — | Rinse | 20.1% |
| Zn Chloride 0.25% | Hexachlorophene 0.1% | Rinse | 34.1% |
| — | Zn TBS 0.125% | Rinse | −2.8%[f] |
| — | Zn TBS/Dylan 0.25%[c] | Rinse | 8.2% |
| — | Quaternary 0.1%[a] | Rinse | 13.4% |
| — | Hexachlorophene 0.1% | Rinse | −13.8%[f] |
| Zn Chloride 0.25% | — | [d]Rinse | 17.6% |
| — | TBS 0.1%[e] | Rinse | 6.6% |

[a]Quaternary is N-methyl-N-(2-hydroxyethyl)-N-(2-hydroxydodecyl)-N-benzyl ammonium chloride.
[b]Zn TBS is the zinc salt of 3,4′5-tribromosalicylanilide.
[c]"Dylan" is polyethylene powder.
[d]The rinse used had the composition of Example 4 but without the quaternary or Zn phenolsulfonate, and with 0.25% ZnCl$_2$(equivalent in Zn content to 0.1% Zn phenolsulfonate.
[e]TBS is 3,4′5-tribromosalicylanilide.
[f]Increase in weight of deposit.
[g]% Reduction in weight of mineralized plaque on the Mylar Strip.

EXAMPLE 3

The oral rinse having the composition shown below retards the formation of dental calculus.

| | % |
|---|---|
| Water | 44.00 |
| Ethanol | 42.00 |
| Glycerol | 12.00 |
| Flavoring | 0.80 |
| Saccharin | 0.10 |
| Zinc sulfate | 1.00 |
| Quaternary* | 0.10 |
| | 100.00 |

*benzyl dimethyl lauryl ammonium chloride

EXAMPLE 4

Following is an example of an oral rinse falling within the invention.

| | % |
|---|---|
| Alcohol, ethyl, U.S.P. 95% | 15.0000 |
| Brij 78 (condensate of stearyl alcohol and 20 molar proportions of ethylene oxide) | 0.1000 |

-continued

|  | % |
|---|---|
| Flavor | 0.1000 |
| Quaternary* | 0.1000 |
| Zn phenolsulfonate | 1.0000 |
| FD&C Blue No. 1 | 0.0001 |
| FD&C Yellow No. 5 | 0.0002 |
| Saccharin | 0.0200 |
| Water | 83.6797 |
|  | 100.0000 |

*N-methyl-N-(2-hydroxyethyl)-N-(2-hydroxydodecyl)-N-benzyl ammonium chloride

EXAMPLE 5

An example of an effective oral rinse composition is shown below.

|  | % |
|---|---|
| Zinc phenolsulfonate | 1.00 |
| Zinc 3,4',5-tribromosalicylanilide | 0.10 |
| Sodium lauryl sulfate | 0.01 |
| Flavor | 0.06 |
| Distilled Water | 98.83 |
|  | 100.00 |

EXAMPLES 6–8

Following are further examples of oral rinse compositions falling within the invention.

| Example No. | 6 | 7 | 8 |
|---|---|---|---|
|  | Percent | Percent | Percent |
| Zinc sulfate | 3.0 |  |  |
| Zinc chloride |  | 0.1 |  |
| Zinc glycerophosphate |  |  | 1.5 |
| 3,4'5-tribromosalicylanilide | 0.03 |  |  |
| Hexachlorophene |  | 0.5 |  |
| 3,4,4'-trichlorocarbanilide |  |  | 0.3 |
| Brij 78 | 0.1 |  | 0.1 |
| Sodium lauryl sulfate |  | 0.05 |  |
| Ethyl alcohol | 20 | 10 | 15 |
| Water | 76.87 | 89.35 | 83.1 |
|  | 100.00 | 100.00 | 100.0 |

EXAMPLE 9

A toothpaste within the invention has the following compositions.

|  | % |
|---|---|
| Silica polishing agent (1) | 15.00 |
| Silica polishing agent (2) | 8.00 |
| Bodying agent | 0.84 |
| Humectants | 36.00 |
| Saccharin | 0.20 |
| Zn phenolsulfonate | 1.00 |
| Zn-3,4'5-tribromosalicylanilide | 0.25 |
| Flavor | 1.30 |
| TiO₂ | 0.50 |
| FD&C Blue No. 1 colorant (1% soln) | 0.02 |
| Alkali (30% solution) | 0.10 |
| Sodium lauryl sulfate-glycerine (3) | 7.00 |
| Water | 29.79 |
|  | 100.00 |

(1) Syloid 63, a silica xerogel having an average particle diameter of 4 – 10 microns.
(2) Syloid 244, a silica aerogel having an average particle diameter of 3 microns.
(3) A solution of 21 parts sodium lauryl sulfate in 79 parts glycerol.
Syloid 63 and Syloid 244 are trademarks of the Davison Chemical Division of the W. R. Grace Company.

EXAMPLES 10–12

Other suitable toothpaste products falling within the invention may be illustrated by the following compositions.

| Example No. | 10 | 11 | 12 |
|---|---|---|---|
|  | Percent | Percent | Percent |
| Dicalcium phosphate dihydrate | 40.0 |  |  |
| Ca pyrophosphate | 5.0 | 45.0 |  |
| Melamine-formaldehyde resin |  |  | 35.0 |
| Na carboxymethylcellulose | 1.0 |  | 1.0 |
| Gum arabic |  | 0.8 |  |
| Glycerol | 20.0 | 7.0 | 10.0 |
| Sorbitol | 10.0 | 13.0 | 25.0 |
| Propylene glycol |  | 5.0 |  |
| ZnSO₄ | 1.5 |  |  |
| Zn acetate |  | 2.0 |  |
| Zn borate |  |  | 3.0 |
| 3,4'5-tribromosalicylanilide | 0.1 |  |  |
| 2,4,4'-trichloro-2'-hydroxy-diphenyl ether |  | 0.2 |  |
| Hexachlorophene |  |  | 0.5 |
| Na lauryl sulfate | 1.5 | 1.0 | 1.2 |
| Water | 20.9 | 26.0 | 24.3 |
|  | 100.0 | 100.0 | 100.0 |

EXAMPLES 13–16

The products of the invention may be in the form of a tooth powder, illustrative examples of which are as follows:

| Example No. | 13 | 14 | 15 | 16 |
|---|---|---|---|---|
|  | Percent | Percent | Percent | Percent |
| Silica polishing agent (1) | 94.0 | 80.8 |  | 4.4 |
| Polyethylene powder (2) |  |  | 92.6 |  |
| Mg Silicate |  | 12.0 |  |  |
| Poly (methyl methacylate) powder |  |  |  | 90.0 |
| Na-lauryl sulfate | 3.0 |  | 3.0 | 2.0 |
| Zinc phenolsulfonate | 1.5 |  |  | 2.0 |
| Zinc sulfate |  | 2.0 | 2.5 |  |
| Zinc TBS (3) | 0.1 |  | 0.3 | 0.2 |
| Hexachlorophene |  | 2.0 |  |  |
| Flavor | 1.4 | 3.0 | 1.3 | 1.2 |
| Saccharin |  | 0.2 | 0.3 | 0.2 |
|  | 100.0 | 100.0 | 100.0 | 100.0 |

(1) Syloid 63, a silica xerogel having an average particle diameter of 4 – 10 microns.
(2) A high density polyethylene powder having an average particle size of 8 – 9 microns.
(3) The zinc derivative of 3,4',5-tribromosalicylanilide.

EXAMPLES 17–18

Below are further examples of toothpaste products falling within the scope of the invention.

| Example No. | 17 | 18 |
|---|---|---|
|  | Percent | Percent |
| Zinc citrate/silica (1) | 27.0 |  |
| Silica (2) | 2.5 | 40.0 |
| Silica (3) | 7.0 | 5.0 |
| Zinc TBS (4) | 0.25 |  |
| Zinc chloride |  | 0.5 |
| Tyrothricin |  | 0.4 |
| Sodium carboxymethylcellulose | 0.9 | 1.0 |
| Chloroform | 0.8 |  |
| Flavoring material | 1.0 | 1.0 |
| TiO₂ | 0.25 |  |
| Saccharin | 0.2 | 0.2 |
| Glycerol | 26.0 | 20.0 |
| Na lauryl sulfate/glycerol (5) | 8.0 | 6.0 |
| Water | 26.1 | 25.9 |

-continued

| Example No. | 17 | 18 |
|---|---|---|
| | Percent | Percent |
| | 100.00 | 100.0 |

(1) 10% zinc citrate, 13.5% Syloid 63, silica xerogel having an average diameter of 4 – 10 microns, and 3.5% water, with a small amount of menthol.
(2) Syloid 63
(3) Syloid 244, a silica aerogel having an average particle diameter of 3 microns.
(4) The zinc derivative of 3,4',5-tribromosalicylanilide.
(5) A solution of 21 parts sodium lauryl sulfate in 79 parts glycerol.

EXAMPLE 19

Twelve subjects brushed their teeth for one minute with a silica-based paste containing 0.25% of the zinc salt of 3,4'5-tribromosalicylanide and 1.0% of zinc phenolsulfonate. Buccal Tissue Counts were made prior to brushing, immediately after brushing and again after elapsed periods of 2 and 3 hours. The results are shown below and indicate that the abovedescribed product greatly inhibits the growth of oral bacteria for a period of at least 3 hours.

| Percent Reduction in Oral Bacteria (Av. for 12 subjects): | |
|---|---|
| Immediately after brushing | 94.7% |
| After 2 hours | 88.0% |
| After 3 hours | 63.8% |

The Buccal Tissue Count is performed as follows:

A sample of Buccal epithelial tissue is obtained from the inside of either cheek by scraping with curette, using several strokes until the cuplike receiver of the curette is filled with a mixture of mucus-epithelial detritus. The tissue is transferred from the curette by agitation into 10 ml. sterile 0.1% peptone water contained in a screw-capped test tube. The contents are shaken throughly, diluted further when necessary, and 1-ml. aliquots in duplicate plated directly into a suitable agar medium. Counts are made after 48 hours incubation at 37° C.

EXAMPLE 20

The following solution provides a 22.7% reduction in calculus by the Mylar Strip Assay described in Example 2.

| Tyrothricin | 0.2% |
|---|---|
| Zinc phenolsulfonate | 1.0% |
| Water | 98.8% |
| | 100.0% |

EXAMPE 21

| Tyrothricin | 0.4% |
|---|---|
| ZnCl$_2$ | 0.5% |
| Water | 99.1% |
| | 100.0% |

The solution of Example 21 provides a 29.2% reduction in calculus when tested by the Rat Assay method. In this Assay, the solution is applied topically by means of a camel's hair brush to the maxillary molar teeth of eight rats. Thirty daily applications are made over a period of 6 weeks. At the end of this time the teeth are scored in comparison with an appropriate control. In determining the calculus score the extent to which various areas of the teeth are covered with deposit are noted and numbers from 0 to 4 assigned accordingly; the greater the coverage of the tooth area, the larger is the assigned number. The percentage reduction is calculus is calculated from thhe total scores of 6 maxillary molar teeth of the treated and untreated animals.

EXAMPLE 22

The following illustrates the ability of an oral rinse of the invention to improve the general gingival health of persons who use the rinse following a brushing with a commercial toothpaste. During the dental examinations for plaque and calculus in the clinical study described in Example 1, note was made of a gingival health of the panel members, and their periodontal condition scored according to the Gingival Index system of Löe and Silness described by Löe, Theilade, and Jensen in J. Periodontology, Volume 36, page 178 (1965).

The results of the gingival examination are shown in Table 3. The numbers are the mean of the additive scores for twelve gingival areas per panel member. The higher the number, the greater is the gingival inflammation.

The results show that the panelists who used an oral rinse of our invention experienced a dramatic improvement in gingival health by the end of the six month test period (phase III).

TABLE 3

| | MEAN GINGIVAL INDEX SCORES | |
|---|---|---|
| | At the End of Phase II | At the End of Phase III |
| | Score | Score |
| 37 Panelists using Pepsodent Toothpaste + a placebo rinse (baseline score of 9.86) | 4.70 | |
| 30 Panelists using Pepsodent Toothpaste + a placebo rinse (baseline score of 9.86) | | 4.59 |
| 36 Panelists using Pepsodent Toothpaste + the oral rinse of Example 1 (baseline score of 9.17) | 3.58 | |
| 31 Panelists using Pepsodent Toothpaste + the oral rinse of Example 1 (baseline score of 9.17) | | 2.47 |

EXAMPLE 23

A suitable oral rinse having a composition within the invention will comprise about 0.2%-0.3% of a material consisting essentially of the zinc derivative of 3,4',5-tribromosalicylanilide attached to an equal weight of polyethylene powder, about 0.75% to about 1.5% zinc phenolsulfonate, the balance to 100% being substantially water. Optionally about 0.1% to about 0.3% total of colorants, flavoring substances, and sweetening substances may be included if desired.

EXAMPLE 24

Following is an example of a dentrifrice falling within the invention.

| | % |
|---|---|
| Silica polishing agent (1) | 12.0 |
| Silica polishing agent (2) | 6.0 |
| Polyethylene powder | 5.0 |
| Zinc citrate | 10.0 |
| Zinc 3,4',5-tribromosalicylanilide | 0.25 |
| Sodium carboxymethylcellulose | 0.8 |
| TiO$_2$ | 0.25 |
| Saccharin | 0.2 |
| Flavoring substance | 1.3 |
| Glycerol | 32.0 |
| Na lauryl sulfate/glycerol (3) | 3.0 |
| Water | 29.2 |
| | 100.00 |

(1) Syloid 63, a silica xerogel having an average particle diameter of 4 – 10 microns.
(2) Syloid 244, a silica aerogel having an average particle diameter of 3 microns.
(3) A solution of 21 parts sodium lauryl sulfate in 79 parts glycerol.
Syloid 63 and Syloid 244 are trademarks of the Davison Chemical Division of the W. R. Grace Company.

EXAMPLE 25

The following mouthwash formulation contains a low level of a soluble zinc compound and a low level of antibacterial agent.

| | % By Weight |
|---|---|
| Zinc chloride$^{(a)}$ | 0.10 |
| 3,4',5-tribromosalicylanilide | 0.03 |
| Ethyl alcohol | 30.00 |
| Water | 69.87 |
| | 100.00 |

$^{(a)}$equivalent to 0.05% Zn

EXAMPLE 26

The following mouthwash formulation contains a slightly soluble zinc compound and an antibacterial agent.

| | % By Weight |
|---|---|
| Zinc citrate$^{(a)}$, Zn$_3$(C$_6$H$_5$O$_7$)$_2$ · 2H$_2$O | 12.4 |
| 2',4,4'-trichloro-2-hydroxydiphenyl ether | 0.5 |
| Ethyl alcohol | 25.0 |
| Water | 62.1 |
| | 100.0 |

$^{(a)}$equivalent to 4% Zn, whole composition basis.

All percentages given herein and in the appended claims are by weight on the whole composition basis.

Many modifications of this invention will be apparent to those skilled in the art, and the invention is to be limited only the scope of the appended claims.

What is claimed is:

1. An oral composition capable of retarding the development of dental calculus consisting essentially of from about 0.05% to about 4% zinc ions and about 0.03% to about 0.5% of a non-toxic, organoleptically acceptable antibacterial agent capable of inhibiting the growth of gram-positive oral microflora for at least about three hours in an orally acceptable medium, said antibacterial agent being selected from the group consisting of 3,4',5-tribromosalicylanilide, the zinc derivative of 3,4',5-tribromosalicylanilide, 3,4',5-trichlorosalicylanilide, the zinc derivative of 3,4',5-trichlorosalicylanilide, 3,5-dibromo-4'-trifluromethylsalicylanilide, the zinc derivative of 3,5-dibromo-4'-trifluoromethylsalicylanilide, 2,4,4'-trichloro-2'-hydroxydiphenyl ether, tyrothricin, chlorhexidine digluconate, chlorhexidine diacetate, quaternary ammonium compounds, wherein said quaternary ammonium compounds are diisobutylphenoxyethoxyethyldimethylbenzylammonium chloride, diisobutylcresoxyethoxyethyldimethylbenzylammonium chloride, N-methyl-N-(2-hydroxyethyl)-N-(2-hydroxydodecyl)N-benzyl ammonium chloride, cetyl trimethylammonium bromide, stearyl trimethylammonium bromide, oleyl dimethylethylammonium bromide, lauryldimethylchlorethoxyethylammonium chloride, lauryldimethylbenzylammonium chloride, alkyl(C$_8$-C$_{18}$) dimethyl (3,4-dichlorobenzyl)-ammonium chloride, lauryl isoquinolinium bromide, N(lauroyloxyethylaminoformylmethyl)pyridinium chloride, and mixtures thereof.

2. An oral composition in accordance with claim 1, wherein said orally acceptable medium comprises ethyl alcohol and water in a ratio of about 1:20 to about 1:2, respectively.

3. An oral composition in accordance with claim 1, wherein said zinc ions are derived from a zinc salt selected from the group consisting of zinc sulfate, zinc chloride, zinc acetate, zinc phenolsulfonate, zinc borate, zinc bromide, zinc nitrate, zinc glycerophosphate, zinc benzoate, zinc carbonate, zinc citrate, zinc hexafluorosilicate, zinc dl-lactate trihydrate, zinc oxide, zinc peroxide, zinc salicylate, zinc silicate, zinc soaps of fatty acids having 8–18 carbon atoms, zinc stannate, zinc tannate, zinc tartrate, zinc titanate, zinc tetrafluoroborate, and mixtures thereof.

4. An oral composition in accordance with claim 1, wherein said antibacterial agent is a bacteriostat.

5. An oral composition in accordance with claim 1, wherein said antibacterial agent is 3,4', 5-tribromosalicylanilide.

6. An oral composition in accordance with claim 1, wherein said antibacterial agent is the zinc derivative of 3,4',5-tribromosalicylanilide.

7. An oral composition in accordance with claim 1, wherein said antibacterial agent is 2',4,4'-trichloro-2-hydroxydiphenyl ether.

8. An oral composition in accordance with claim 1, wherein said zinc ions are derived from zinc phenolsulfonate and said antibacterial agent is the zinc derivative of 3,4',5-tribromosalicylanilide.

9. An oral composition in accordance with claim 1, wherein said antibacterial agent is selected from chlorohexidine digluconate and chlorhexidine diacetate.

10. An oral composition capable of retarding the development of plaque and dental calculus consisting essentially of zinc ions, and antibacterial agent and a particulate inorganic dental polishing agent, said zinc ions being present in the proportion of about 0.05% to about 4% and being furnished by a soluble zinc compound, said antibacterial agent being present within the range of about 0.03% to about 0.5%, and capable of inhibiting the growth of gram-positive oral microflora at least about three hours being selected from the group consisting of 3,4',5-tribromosalicylanilide, the zinc derivative of 3,4',5-tribromosalicylanilide, 3,4',5-trichlorosalicylanilide, the zinc derivative of 3,4',5-trichlorosalicylanilide, 3,5-dibromo-4'-trifluoromethylsalicylanilide, the zinc derivative of 3,5-dibromo-4'-trifluoromethylsalicylanilide, 2,4,4'-trichloro-2'-hydroxydiphenyl ether, tyrothricin, chlorhexidine digluconate, chlorhexidine diacetate, quaternary ammonium compounds wherein said quaternary ammonium compounds are diisobutylphenoxyethoxyethyldimethylbenzylammonium chloride, diisobutylcresoxyethoxyethyldimethylbenzylammonium chloride, N-methyl-N-(2-hydroxyethyl)-N-(2-hydroxydodecyl)N-benzylammonium chloride, cetyl trimethylammonium bromide, stearyl trimethylammonium bromide, oleyl dimethylethylammonium bromide, lauryldimethylchlorethoxyethylammonium chloride, lauryldimethylbenzylammonium chloride, alkyl($C_8$-$C_{18}$) dimethyl (3,4-dichlorobenzyl)-ammonium chloride, lauryl isoquinolinium bromide, N(lauroyloxyethylaminoformylmethyl)pyridinium chloride and mixtures thereof.

11. An oral composition in accordance with claim 10, wherein said zinc ions are present in the proportion of about 0.2% to about 1.5%.

12. An oral composition in accordance with claim 10, wherein said zinc ions are present within the range of about 0.05% to about 0.5%.

13. An oral composition in accordance with claim 10, wherein said zinc ions are derived from phenolsulfonate and said antibacterial agent is the zinc derivative of 3,4',5-tribromosalicylanilide.

14. An oral composition in accordance with claim 10, wherein said zinc ions are derived from zinc citrate and said antibacterial agent is the zinc derivative of 3,4',5-tribromosalicylanilide.

15. An oral composition in accordance with claim 10, wherein said zinc ions are derived from zinc citrate and wherein said zinc citrate is attached to particles of said particulate dental polishing agent.

16. A method for retarding the development of dental calculus, which comprises contacting tooth surfaces with an anticalculus composition comprising from about 0.05% to about 1.5% zinc ions, and about 0.03% to about 0.5% of a non-toxic, organoleptically acceptable antibacterial agent capable of inhibiting the growth of gram-positive oral microflora for at least about three hours, in an orally acceptable medium, said antibacterial agent being selected from the group consisting of 3,4',5-tribromosalicylanilide, the zinc derivative of 3,4',5-tribromosalicylanilide, 3,4',5-trichlorosalicylanilide, the zinc derivative of 3,4',5-trichlorosalicylanilide, 3,5-dibromo-4'-trifluoromethylsalicylanilide, the zinc derivative of 3,5-dibromo-4'-trifluoromethylsalicylanilide, 2,4,4'-trichloro-2'-hydroxydiphenyl ether, tyrothricin, chlorhexidine digluconate, chlorhexidine diacetate, quaternary ammonium compounds wherein said quaternary ammonium compounds are diisobutylphenoxyethoxyethyldimethylbenzylammonium chloride, diisobutylcresoxyethoxyethyldimethylbenzylammonium chloride, N-methyl-N-(2-hydroxyethyl)-N-(2-hydroxydodecyl)-N-benzyl ammonium chloride, cetyl trimethylammonium bromide, stearlyl trimethylammonium bromide, oleyl dimethylethylammonium bromide, lauryldimethylchloretoxylethylammonium chloride, lauryldimethylbenzylammonium chloride, alkyl($C_8$-$C_{18}$)dimethyl(3,4-dichlorobenzyl)-ammonium chloride, lauryl isoquinolinium bromide, N(lauroyloxyethylaminoformylmethyl)pyridinium chloride and mixtures thereof.

17. A method in accordance with claim 16 wherein said zinc ions are derived from zinc phenolsulfonate and said antibacterial agent is the zinc derivative of 3,4',5-tribromosalicylanilide.

18. An oral composition in accordance with claim 1 wherein said antibacterial agent is a ($C_{8-18}$) alkyl pyridinium bromide or a ($C_{8-18}$) alkyl pyridinium chloride.

19. An oral composition in accordance with claim 10 wherein said antibacterial agent is a ($C_{8-18}$) alkyl pyridinium bromide or a ($C_{8-18}$) alkyl pyridinium chloride.

20. A method in accordance with claim 16 wherein said antibacterial agent is a ($C_{8-18}$) alkyl pyridinium bromide, or a ($C_{8-18}$) alkyl pyridinium chloride.

* * * * *